United States Patent [19]

Panzer et al.

[11] 4,137,416

[45] Jan. 30, 1979

[54] 2-ACYLAMIDOETHYL-2-IMIDAZOLINES

[75] Inventors: Hans P. Panzer, Stamford; Kenny U. Acholonu, Bridgeport, both of Conn.

[73] Assignee: American Cyanamid Company, Stamford, Conn.

[21] Appl. No.: 867,252

[22] Filed: Jan. 5, 1978

[51] Int. Cl.² ............................................. C07D 233/26
[52] U.S. Cl. ........................................................ 548/353
[58] Field of Search ........................................... 548/353

[56] References Cited

U.S. PATENT DOCUMENTS 3,995,044  11/1976  Kabbe et al. .................. 548/353 X

OTHER PUBLICATIONS

Dickinson et al., Chemical Abstracts, vol. 77 (1972) 159,986n.

*Primary Examiner*—Richard Raymond
*Attorney, Agent, or Firm*—William J. van Loo

[57] ABSTRACT

2-acylamidoethyl-2-imidazolines are disclosed which are desirable precursors for 2-vinyl-2-imidazolines.

5 Claims, No Drawings

2-ACYLAMIDOETHYL-2-IMIDAZOLINES

CROSS-REFERENCE TO RELATED APPLICATIONS:

This application is related to applications Ser. Nos. 867,251 and 867,255, filed on even date herewith. The instant application relates to 2-acylamidoethyl-2-imidazolines. Ser. No. 867,251 relates to a process for preparation thereof and Ser. No. 867,255 relates to a process for preparing 2-vinyl-2-imidazolines by cleavage of 2-acylamido-2-imidazolines.

This invention relates to precursors useful for preparing vinylimidazolines by cleavage of the precursors. More particularly, this invention relates to 2-acylamidoethyl-2-imidazolines.

The need for high-efficiency products for use in the treatment of aqueous suspension of solids has continued to grow in recent years because of the increasing awareness of the environmental pollution caused by such substances and other considerations. Accordingly, there have been increased efforts expended in attempts to provide such products which can be used to facilitate the dewatering of aqueous suspensions of organic, or mixtures of organic and inorganic, materials such as distillery wastes, fermentation wastes, wastes from paper manufacturing plants, dye plant wastes and sewage suspensions such as digested sludges, activated sludges, or raw and primary sludges from sewage treatment plants as well as a host of other suspension types.

The more recent and more successful materials used in the treatment of such suspensions have been amidine or imidazoline polymers, see U.S. Pat. Nos. 3,406,139; 3,450,646; 3,576,740 and 3,666,705. Such polymers are very effective materials for use in the treatment of industrial wastes. The polymers are produced, however, by the treatment of corresponding nitrite polymers and are therefore governed by the structure of the nitrile polymers. Furthermore, conversion of the nitrile polymers to the imidazoline or amidine form does not reach 100% and therefore a portion of the resultant polymer is in improper form to function in water treating capacity.

Prior attempts to obviate these difficulties have included rearrangement of the groups present in the nitrile charge polymer and the attempted production of unsaturated imidazolines which may be homopolymerized or copolymerized into more active imidazoline polymers. However, attempts to produce intermediates, from which the unsaturated imidazolines may be prepared, have proven unsuccessful. Furthermore, attempts to follow the teachings of U.S. Pat. No. 3,210,371 resulted only in the production of undesired polymeric material and the teachings of Oxley et al., J. Chem. Soc. 1947, pages 497–505, also resulted in the recovery of undesired polymeric products.

Recent developments are typified by U.S. Pat. Nos. 4,006,247 and 4,007,200. In U.S. Pat. No. 4,007,200, there are disclosed intermediates which require numerous preparative steps which are difficult to perform, thus complicating processing and reducing yields of the intermediate. In U.S. Pat. No. 4,006,247, it is disclosed that the intermediates of U.S. Pat. No. 4,007,200 can be cracked to provide unsaturated imidazolines. However, the intermediate is unstable in cracking, thus reducing yields of unsaturated imidazoline. The cracking process is difficult to perform and undesirable.

There continues to exist the need for improved intermediates for unsaturated imidazolines which are readily prepared and are easily converted to the desired unsaturated imidazolines by simple processing. Such a provision would fulfill a long-felt need and constitute a notable advance in the art.

In accordance with the present invention, there are provided compounds of the structure:

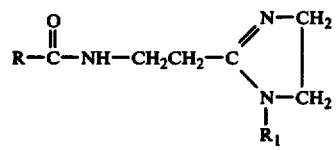

wherein R is an alkyl group of about 1 to 5 carbon atoms and $R_1$ is hydrogen or an alkyl group of about 1 to 5 carbon atoms.

Compounds of the present invention are stable intermediates which are readily prepared and are readily cleaved to provide vinylimidazolines. Their ready processability results in savings in materials, processing steps, and processing costs while providing good yields of monomeric product which can be readily processed to the desired polymers for the various uses previously mentioned.

As indicated, the compounds of the present invention have the structure:

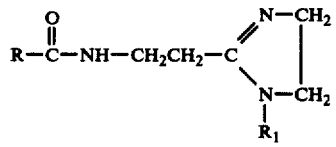

wherein R is an alkyl group of about 1 to 5 carbon atoms and $R_1$ is hydrogen or an alkyl of about 1 to 5 carbons. When the compounds are cleaved, an acylamide is provided as well as the vinylimidazoline. It is desirable that the acylamide have a higher boiling point than the vinylimidazoline so as to provide easier separation of these cleavage products. Typical compounds of the present invention are 2-acetamidoethyl-2-imidazoline, 2-propionamidoethyl-2-imidazoline, 2-butyramidoethyl-2-imidazolidine, and the like.

The compounds of the present invention which are 2-acylamidoethyl-2-imidazolines, are conveniently prepared starting with a suitable 2-cyanoethylacylamide. This starting compound type is known in the art and is readily prepared by reacting acrylonitrile with an acylamide in the presence of a strong alkali. The reaction is described in the Chemistry of Acrylonitrile, IV Cyanoethylation of Active Hydrogen Groups, Bruson and Riener, J. Am. Chem. Soc., 65, page 23 (1943). This reaction is given by the equation

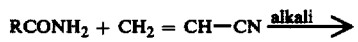

For the purposes of the present invention, R is an alkyl group of about 1 to 5 carbon atoms.

Using a selected 2-cyanoethylacylamide as described, the desired 2-acylamidoethyl-2-imidazoline of the present invention is prepared by reaction thereof with an ethylenediamine of the structure $R_1HN\text{-}CH_2CH_2\text{-}NH_2$, wherein $R_1$ is hydrogen or an alkyl group of about 1 to 5 carbon atoms, preferably in the presence of a suitable catalyst. A preferred catalyst is sulfur. The reaction is carried out at an elevated temperature to minimize reaction time but at a temperature safely below that at which decomposition occurs. Reaction is quite rapid, generally 90 minutes or less at 115° C. A solvent may be used if desired but reaction can be effected in the absence of solvent. The crude product obtained is readily purified by recrystallization, for example, and yields of pure product are 70% or higher. The reaction follows the equation:

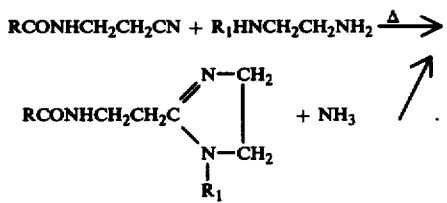

The reactants are generally used in equal molar amounts. If a catalyst is employed, it is used in an effective amount. Preferably, sulfur is used at a concentration of about 0.5 to 1.0 weight percent based on the weight of reactants. As indicated, a solvent may be used if desired and, if used, should generally be in an amount providing suitable fluidity to the reaction mixture. A preferred solvent is toluene.

The compounds of the present invention are readily cleaved to provide the desired vinylimidazoline monomer. Cleavage can be effected by heating the intermediate in the presence of suitable cracking agents in a reaction flask and distilling off and recovering the cleavage products. Separation of the vinylimidazoline monomer by suitable procedure, such as by preparing a salt of the vinylimidazoline. The cleavage reaction, which forms the desired vinylimidazoline monomer, is given by the equation:

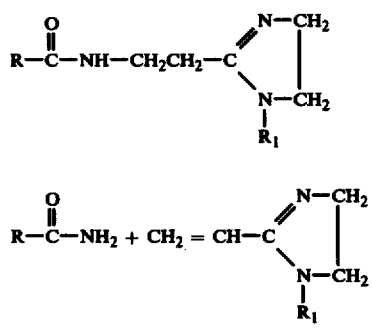

wherein R and $R_1$ have the meaning previously given.

The invention is more fully illustrated by the examples which follow wherein all parts and percentages are by weight unless other specified.

EXAMPLE 1

Preparation of 2-acetamidoethyl-2-imidazoline

To a 500 ml. round-bottomed flask equipped with a thermometer and reflux condenser were added 129.00 grams (1.15 mol) of 2-cyanoethylacetamide, 67.7 grams (1.13 mol) of ethylenediamine and 1.5 grams of sulfur. The reaction mixture was heated to 115° C. and held at that temperature for 90 minutes. Solidification of the reaction mixture occurred on cooling. The crude product weight 158 grams. It was recrystallized from 80 mol. of 2-propanol. 142 grams of pure product were obtained representing a yield of 81.2%. The product had a melting point of 137°-139° C.

EXAMPLE 2

Preparation of 2-Acetamidoethyl-2-(1-methyl)imidazoline

To a 100 ml round-bottomed flask equipped with a thermometer and reflux condenser were added 22.4 grams (0.2 mol) of 2-cyanoethylacetamide, 14.8 grams (0.2 mol) of N-methylethylenediamine, 0.3 gram of sulfur, and 30 mol of toluene. The reaction mixture was heated and held at 110° C. for 3 hours. The solid product which formed was separated from the solvent after cooling by filtration. The nuclear magnetic resonance analysis of the product was consistent with 2-acetamidoethyl-2-(1-methyl)-imidazoline. The yield was 25 grams or 73.9%.

EXAMPLE 3

Cleavage of 2-Acetamidoethyl-2-imidazoline

To a 250 ml round-bottomed flask equipped with a distillation head, vacuum take-off adapter, and a receiver were added 22.2 grams (0.144 mol) of 2-acetamidoethyl-2imidazoline as prepared in Example 1, 70 grams of Carbowax 700, 4 grams of potassium hydroxide, 4.8 milligrams of Cupferon and 0.5 gram of phenothiazine. The mixture was thoroughly mixed and heated to 200° C. at a pressure equivalent to 0-5 millimeters of mercury. At 80°-125° C. 2-vinyl-2-imidazoline codistilled with acetamide. 15.4 grams of product was isolated. NMR analysis of the bisulfate salt of 2-vinyl-2-imidazoline indicated a yield of 60%.

The recovered 2-vinyl-2-imidazoline was readily polymerized in aqueous solution to provide a high molecular weight polymer which showed excellent properties as a flocculant and dewatering agent.

EXAMPLES 4 – 7

Following the procedure of Example 2 in every material detail, a series of preparations were made. In each preparation an equivalent molar amount of 2-cyanoethylacylamide and an ethylenediamine were used in place of that used in Example 2. In each instance, a corresponding 2-acylamidoethyl-2-imidazoline was obtained in good yield and having a structure consistent with the desired product. The 2-acylamidoethyl-2-imidazolines produced were cleaved to the corresponding 2-vinylimidazolines following the procedure of Example 3. The reactants and products obtained are given below along with the example number.

| Example No. | 2-cyanoethyl-acylamide (R-group) | Ethylene Diamine ($R_1$-group) | Product |
|---|---|---|---|
| 4 | $C_2H_5-$ | H | $C_2H_5CONHCH_2CH_2-C\begin{smallmatrix}N-CH_2\\ \\N-CH_2\\|\\H\end{smallmatrix}$ |
| 5 | $C_3H_7-$ | $CH_3-$ | $C_3H_7CONHCH_2CH_2-C\begin{smallmatrix}N-CH_2\\ \\N-CH_2\\|\\CH_3\end{smallmatrix}$ |
| 6 | $C_2H_5-$ | $C_2H_5-$ | $C_2H_5CONHCH_2CH_2-C\begin{smallmatrix}N-CH_2\\ \\N-CH_2\\|\\C_2H_5\end{smallmatrix}$ |
| 7 | $CH_3-$ | $C_3H_7-$ | $CH_3CONHCH_2CH_2-C\begin{smallmatrix}N-CH_2\\ \\N-CH_2\\|\\C_3H_7\end{smallmatrix}$ |

We claim:
1. A compound of the structure

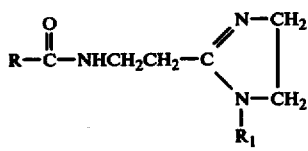

wherein R is an alkyl group of about 1 to 5 carbon atoms and $R_1$ is hydrogen or alkyl of about 1 to 5 carbon atoms.

2. A compound of claim 1 wherein R is methyl and $R_1$ is hydrogen.

3. A compound of claim 1 wherein R is methyl and $R_1$ is methyl.

4. A compound of claim 1 wherein R is ethyl and $R_1$ is hydrogen.

5. A compound of claim 1 wherein R is propyl and $R_1$ is methyl.